United States Patent
Kim et al.

(10) Patent No.: US 9,845,288 B2
(45) Date of Patent: Dec. 19, 2017

(54) T-BUTYLKETONE BINAPHTHOL DERIVATIVE AND METHOD OF PREPARING THE SAME

(71) Applicants: EWHA UNIVERSITY—INDUSTRY COLLABORATION FOUNDATION, Seoul (KR); AMINOLOGICS CO., LTD., Seoul (KR)

(72) Inventors: Kwan Mook Kim, Seoul (KR); Haofei Huang, Seoul (KR)

(73) Assignees: EWHA UNIVERSITY-INDUSTRY COLLABORATION FOUNDATION (KR); AMINOLOGICS CO., LTD. (KR)

(*) Notice: Subject to any disclaimer, the term of this patent is extended or adjusted under 35 U.S.C. 154(b) by 0 days.

(21) Appl. No.: 15/119,874

(22) PCT Filed: Feb. 17, 2015

(86) PCT No.: PCT/KR2015/001612
§ 371 (c)(1),
(2) Date: Aug. 18, 2016

(87) PCT Pub. No.: WO2015/126150
PCT Pub. Date: Aug. 27, 2015

(65) Prior Publication Data
US 2017/0050923 A1    Feb. 23, 2017

(30) Foreign Application Priority Data
Feb. 19, 2014 (KR) .................... 10-2014-0019021

(51) Int. Cl.
*C07C 275/32* (2006.01)

(52) U.S. Cl.
CPC ........ *C07C 275/32* (2013.01); *C07B 2200/07* (2013.01)

(58) Field of Classification Search
None
See application file for complete search history.

(56) References Cited

U.S. PATENT DOCUMENTS

2006/0173211 A1* 8/2006 Kim .................... C07C 213/10
562/439

FOREIGN PATENT DOCUMENTS

| KR | 10-2006-0088489 | 8/2006 |
| KR | 10-2010-0106221 | 10/2010 |
| KR | 10-2014-0033581 | 3/2014 |

OTHER PUBLICATIONS

Huang 2014 ("Highly enantioselective extraction of underivatized amino acids by the uryl-pendant hydenyl-binol ketone" Chemistry—A European Journal, vol. 20, 2014, p. 2895-2900).*

(Continued)

*Primary Examiner* — Jafar Parsa
*Assistant Examiner* — Amy C Bonaparte
(74) *Attorney, Agent, or Firm* — Riverside Law LLP

(57) ABSTRACT

The present disclosure relates to a t-butylketone binaphthol derivative and a method of preparing the same, the t-butylketone binaphthol derivative being a high-efficiency chiral extracting agent which has a very high chiral selectivity enabling to extract an amino acid from an aqueous solution phase to an organic layer and to facilitate its hydrolysis, and enabling a continuous reuse of the organic layer.

9 Claims, 2 Drawing Sheets

2-D-Ala

2-L-Ala

(56) References Cited

OTHER PUBLICATIONS

International Search Report of PCT/KR2015/001612 dated Jun. 1, 2015.
Haofei Huang et al., "Enantioselective Liquid-Liquid Extractions of Underivatized General Amino Acids with a Chiral Ketone Extractant", Journal of the American Chemical Society, Jan. 14, 2013, vol. 135, pp. 2653-2658.
Raju Nandakumar et al., "A chiral ketone for enantioselective recognition of 1,2-amino alcohols", Tetrahedron Letters, Aug. 2, 2007, vol. 48, pp. 6582-6585.

* cited by examiner

2-D-Ala

2-L-Ala

T-BUTYLKETONE BINAPHTHOL DERIVATIVE AND METHOD OF PREPARING THE SAME

CROSS-REFERENCE TO RELATED APPLICATIONS

This application claims priority from PCT application no. PCT/KR15/001612, filed Feb. 17, 2015 and Korean patent application no. KR 10-2014-0019021, filed Feb. 19, 2014, each of which is hereby incorporated by reference in their entirety.

TECHNICAL FIELD

The present disclosure relates to a t-butylketone binaphthol derivative and a method of preparing the same, the t-butylketone binaphthol derivative being a high-efficiency chiral extracting agent which has a very high chiral selectivity enabling to extract an amino acid from an aqueous solution phase to an organic layer and to facilitate its hydrolysis, and enabling a continuous reuse of the organic layer.

BACKGROUND

Optically pure amino acids are used as a ligand of asymmetric catalysts, or may be widely utilized as starting materials or intermediates necessary to synthesize a variety of medical products and physiologically active materials, and are thus regarded as a very important compound from the industrial point of view [Helmchen, G.; Pfaltz, A., Acc. Chem. Res. 2000, 33, 336-345].

It has been known that amino acids are economically produced via fermentation. However, amino acids resulting from fermentation are limited to only L-amino acids among natural amino acids. Although optically pure D-amino acids and non-natural amino acids are produced via an enzyme process or an optical resolution process, they cost a lot to prepare and thus their unit prices are about 5 times to 10 times higher than those of natural L-amino acids resulting from fermentation as well as their mass production is difficult to achieve. Therefore, there have been efforts to achieve economical mass-production of amino acids [Maruoka, K.; Ooi, T. Chem. Rev. 2003, 103, 3013].

As a part of the efforts, the present inventors have developed a method of transforming L-amino acid into D-amino acid by recognizing chirality of aminoalcohol and amino acid via an imine bond using a binaphthol derivative having an aldehyde group as represented by the following chemical formula [(a) Park, H.; Kim, K. M.; Lee, A.; Ham, S.; Nam, W.; Chin, J., J. Am. Chem. Soc. 2007, 129, 1518-1519; (b) Kim, K. M.; Park, H.; Kim, H.; Chin, J.; Nam, W., Org. Lett. 2005, 7, 3525-3527].

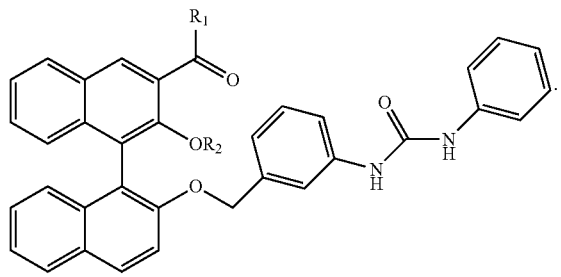

[Binaphthol Derivative]

Meanwhile, an enantioselective liquid-liquid extraction (ELLE) process is a simple process and easy to scale up and also enables the production of amino acids at low costs. Thus, the production of optically pure amino acids by the ELLE process has been studied for a long time [Schuur, B.; Verkuijl, B. J. V.; Minnaard, A. J.; de Vries, J. G.; Heeres, H. J.; Feringa, B. L. Org., Biomol. Chem. 2011, 9, 36-51]. A very important factor in ELLE of amino acids is the development of a chiral extracting agent with a high selectivity. Numerous chiral extracting agents for amino acids have been developed so far, but they have a selectivity of from about 2/1 to about 5/1. Therefore, it is desperate to develop a chiral extracting agent having a high selectivity to perform the ELLE of amino acids [(a) Amato, M. E.; Ballistreri, F. P.; D'Agata, S.; Pappalardo, A.; Tomaselli, G. A.; Toscano, R. M.; Sfrazzetto, G. T. Eur. J., Org. Chem. 2011, 28, 5674-5680; (b) Colera, M.; Costero, A. M.; Gavina, P.; Gil, S., Tetrahedron: Asymmetry 2005, 16, 2673-2679].

Recently, the present inventors filed a patent application relating to a method of using a binaphthol derivative which is described above as a chiral converting agent for amino acids, as a chiral extracting agent for the ELLE of amino acids (Korean Patent Application No. 10-2009-0032956). This binaphthol derivative enables the extraction of amino acids from an aqueous solution layer to an organic layer by forming an imine and has a chiral selectivity of from about 5/1 to about 20/1 depending on the kind of an amino acid, and the chiral selectivity is higher than those of previously developed chiral extracting agents.

The present disclosure was achieved in the development of a chiral extracting agent having a remarkably higher chiral selectivity than this previous binaphthol derivative.

DETAILED DESCRIPTION OF THE INVENTION

Problems to be Solved by the Invention

Accordingly, the present disclosure provides a t-butylketone binaphthol derivative and a method of preparing the same, the t-butylketone binaphthol derivative being a high-efficiency chiral extracting agent which has a very high chiral selectivity enabling to extract an amino acid from an aqueous solution phase to an organic layer and to facilitate its hydrolysis, and enabling a continuous reuse of the organic layer.

However, problems to be solved by the present disclosure are not limited to the above-described problems. Although not described herein, other problems to be solved by the present disclosure can be clearly understood by those skilled in the art from the following descriptions.

Means for Solving the Problems

In accordance with a first aspect of the present disclosure, there is provided a t-butylketone binaphthol derivative represented by the following Chemical Formula 1:

[Chemical Formula 1]

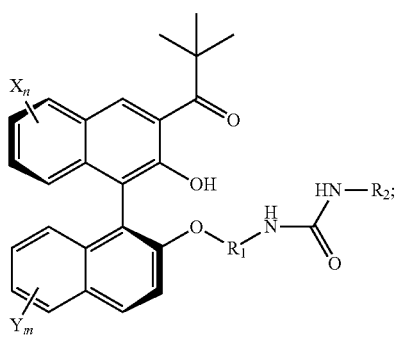

in the above Chemical Formula 1,

X is independently selected from the group consisting of hydrogen; a halogen; amino; nitro; cyano; formyl; carboxyl; a $C_{1-10}$ alkyl substituted or unsubstituted with one or more substituents selected from the group consisting of a halogen, hydroxyl, amino, cyano, nitro, and a $C_{6-10}$ aryl; a $C_{1-10}$ alkylcarbonyl; a $C_{6-10}$ to aryl; and a $C_{1-10}$ alkoxy;

Y is independently selected from the group consisting of hydrogen; a halogen; amino; nitro; cyano; formyl; carboxyl; a $C_{1-10}$ alkyl substituted or unsubstituted with one or more substituents selected from the group consisting of a halogen, hydroxyl, amino, cyano, nitro, and a $C_{6-10}$ aryl; a $C_{1-10}$ alkylcarbonyl; a $C_{6-10}$ aryl; and a $C_{1-10}$ alkoxy;

each of n and m independently represents an integer of from 0 to 5; and each of $R_1$ and $R_2$ independently represents a $C_{1-5}$ straight or branched alkyl substituted or unsubstituted with a halogen or OH; a $C_{3-10}$ cycloalkyl substituted or unsubstituted with a halogen or OH; a $C_{2-5}$ straight or branched alkenyl substituted or unsubstituted with a halogen or OH; a $C_{2-5}$ straight or branched alkynyl substituted or unsubstituted with a halogen or OH; or an aryl substituted or unsubstituted with a halogen or OH.

In accordance with a second aspect of the present disclosure, there is provided a chiral extracting agent comprising the t-butylketone binaphthol derivative represented by Chemical Formula 1 according to the first aspect of the present disclosure.

In accordance with a third aspect of the present disclosure, there is provided an optical resolution method of a racemic amino acid, comprising: using a chiral extracting agent including a t-butylketone binaphthol derivative represented by Chemical Formula 1 according to the first aspect of the present disclosure.

Effects of the Invention

According to the present disclosure, a novel t-butylketone binaphthol derivative has a remarkably higher chiral selectivity and a higher solubility than the conventional binaphthol derivatives, and thus, the novel t-butylketone binaphthol derivative can be very useful for enantioselective liquid-liquid extraction of amino acids.

BEST MODE FOR CARRYING OUT THE INVENTION

Figure 1A:
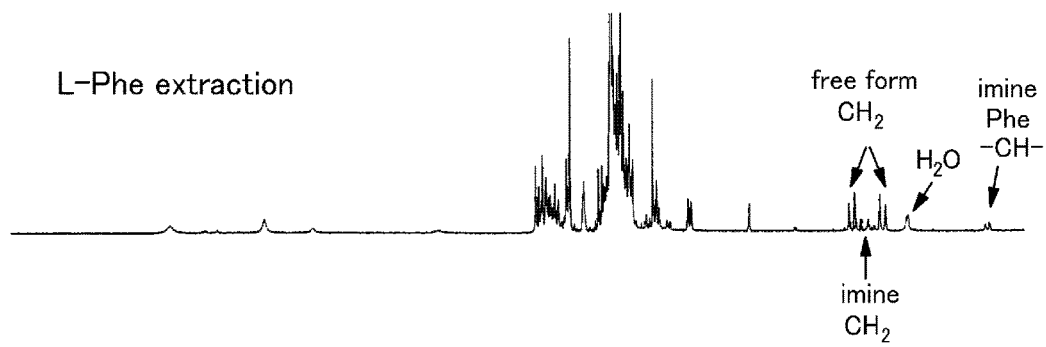
FIG. 1A shows a $^1$H NMR (nuclear magnetic resonance) spectrum of an organic layer after liquid-liquid extraction of an aqueous solution layer using L-Phe only in an enantioselective liquid-liquid extraction (ELLE) experiment with phenylalanine in accordance with an example of the present disclosure.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "alkyl (group)" may respectively include a linear or branched, saturated or unsaturated $C_{1-20}$ alkyl (group), and may include, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, acosanyl, or all the possible isomers thereof, but may not be limited thereto.

Through the whole document, the term "alkenyl (group)" refers to a monovalent hydrocarbon group including at least one carbon-carbon double bond in an alkyl (group) having two or more carbon atoms among the above-described alkyl (group), and may include a linear or branched $C_{2-20}$ alkenyl (groups), but may not be limited thereto.

Through the whole document, the term "alkynyl (group)" refers to a monovalent hydrocarbon group including at least one carbon-carbon triple bond in an alkyl (group) having two or more carbon atoms among the above-described alkyl (group), and may include a linear or branched $C_{2-20}$ alkynyl (groups), but may not be limited thereto.

Through the whole document, the term "aryl (group)" refers to a monovalent functional group formed by the removal of one hydrogen atom from one or more rings of an arene, and may include, for example, phenyl, biphenyl, terphenyl, naphthyl, anthryl, phenanthryl, pyrenyl, or all the possible isomers thereof, but may not be limited thereto. The arene may refer to a hydrocarbon group having an aromatic ring, and includes a monocyclic and polycyclic hydrocarbon groups. The polycyclic hydrocarbon group includes one or more aromatic rings and includes an aromatic or non-aromatic ring as an additional ring, but may not be limited thereto.

Through the whole document, the term "cycloalkyl (group)" refers to a monovalent functional group having a saturated hydrocarbon ring, and may include a $C_{3-8}$ cycloalkyl (groups), for example, cyclopropyl, cylcobutyl, cyclopentyl, cyclohexyl, cycloheptyl, cyclooctyl, or all the possible isomers thereof, but may not be limited thereto.

Through the whole document, the term "alkoxy (group)" refers to the above-defined alkyl group bonded to an oxygen atom, and may include a $C_{1-20}$ alkoxy (groups), for example, methoxy, ethoxy, propoxy, butoxy, pentoxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, acosanyloxy, or all the possible isomers thereof, but may not be limited thereto.

Through the whole document, the term "halo group" refers to a halogen element from Group XVII of the periodic table included as a functional group in a compound, and the halogen element may include, for example, F, Cl, Br, or I, but may not be limited thereto.

Through the whole document, the term "alkali metal" refers to a metal from Group I of the periodic table, and may include Li, Na, K, Rb, Cs, or Fr, but may not be limited thereto.

Hereinafter, embodiments of the present disclosure will be described in detail. However, the present disclosure may not be limited to the following embodiments.

In accordance with a first aspect of the present disclosure, there is provided a t-butylketone binaphthol derivative represented by the following Chemical Formula 1:

[Chemical Formula 1]

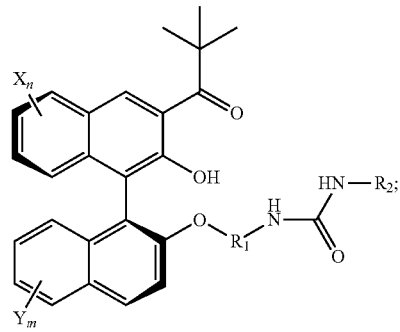

in the above Chemical Formula 1,

X is independently selected from the group consisting of hydrogen; a halogen; amino; nitro; cyano; formyl; carboxyl; a $C_{1-10}$ alkyl substituted or unsubstituted with one or more substituents selected from the group consisting of a halogen, hydroxyl, amino, cyano, nitro, and a $C_{6-10}$ aryl; a $C_{1-10}$ alkylcarbonyl; a $C_{6-10}$ aryl; and a $C_{1-10}$ alkoxy;

Y is independently selected from the group consisting of hydrogen; a halogen; amino; nitro; cyano; formyl; carboxyl; a $C_{1-10}$ alkyl substituted or unsubstituted with one or more substituents selected from the group consisting of a halogen, hydroxyl, amino, cyano, nitro, and a $C_{6-10}$ aryl; a $C_{1-10}$ alkylcarbonyl; a $C_{6-10}$ aryl; and a $C_{1-10}$ alkoxy;

each of n and m independently represents an integer of from 0 to 5; and each of $R_1$ and $R_2$ independently represents a $C_{1-5}$ straight or branched alkyl substituted or unsubstituted with a halogen or OH; a $C_{3-10}$ cycloalkyl substituted or unsubstituted with a halogen or OH; a $C_{2-5}$ straight or branched alkenyl substituted or unsubstituted with a halogen or OH; a $C_{2-5}$ straight or branched alkynyl substituted or unsubstituted with a halogen or OH; or an aryl substituted or unsubstituted with a halogen or OH.

In accordance with an embodiment of the present disclosure, the t-butylketone binaphthol derivative may include a compound represented by the following Chemical Formula 2, but may not be limited thereto:

[Chemical Formula 2]

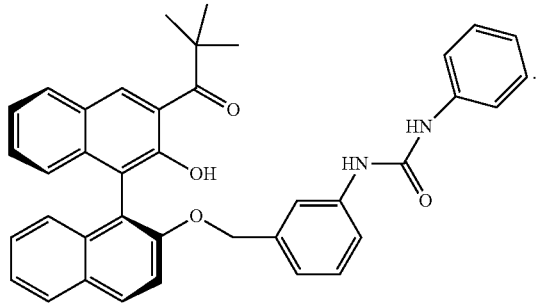

In the present disclosure, the t-butylketone binaphthol derivative represented by Chemical Formula 1 is used in an optically pure form. The t-butylketone binaphthol derivative represented by Chemical Formula 1 is in a S-form, but its enantiomer, a R-form can be used.

Although the compound represented by Chemical Formula 2 may be synthesized by any method, a method represented by the following Reaction Formula 1 can be typically used:

[Reaction Formula 1]

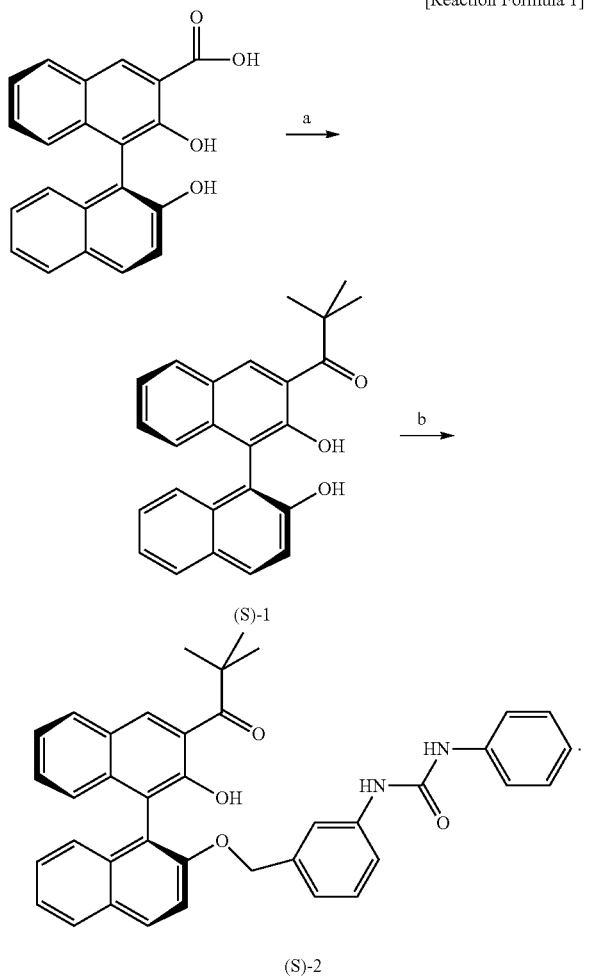

As the reagents and conditions, a represents t-butyl-lithium/THF, 0° C. and 6 h, and b represents 3-phenyluryl-benzyl bromide, NaH/DMF and 12 h.

In accordance with a second aspect of the present disclosure, there is provided a chiral extracting agent comprising the t-butylketone binaphthol derivative represented by Chemical Formula 1 according to the first aspect of the present disclosure.

In accordance with an embodiment of the present disclosure, the t-butylketone binaphthol derivative may have a chiral selectivity of about 95% or more, but may not be limited thereto. For example, the t-butylketone binaphthol derivative may have a chiral selectivity of about 95% or more, about 96% or more, about 97% or more, about 98% or more, or about 99% or more, but may not be limited thereto.

In accordance with an embodiment of the present disclosure, the t-butylketone binaphthol derivative may be in a S-form or R-form, but may not be limited thereto.

In accordance with an embodiment of the present disclosure, the t-butylketone binaphthol derivative may be used for L/D optical conversion of an amino acids, but may not be limited thereto.

In accordance with an embodiment of the present disclosure, the t-butylketone binaphthol derivative may include carbonyl group (C=O) that binds with an amino acid to form an imine, but may not be limited thereto.

In accordance with a third aspect of the present disclosure, there is provided an optical resolution method of a racemic amino acid, comprising: using a chiral extracting agent including a t-butylketone binaphthol derivative represented by the following Chemical Formula 1:

[Chemical Formula 1]

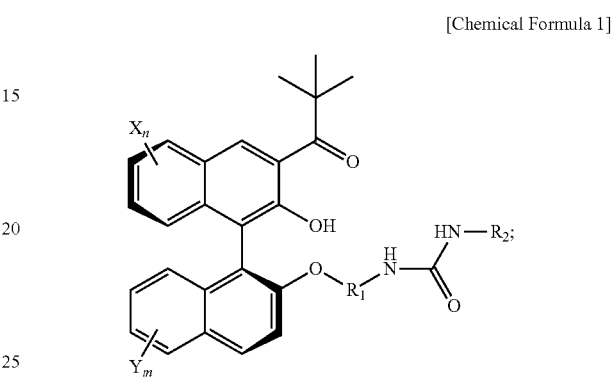

in the above Chemical Formula 1,

X is independently selected from the group consisting of a hydrogen; a halogen; amino; nitro; cyano; formyl; carboxyl; a $C_{1-10}$ alkyl substituted or unsubstituted with one or more substituents selected from the group consisting of a halogen, hydroxyl, amino, cyano, nitro, and a $C_{6-10}$ aryl; a $C_{1-10}$ alkylcarbonyl; a $C_{6-10}$ aryl; and a $C_{1-10}$ alkoxy;

Y is independently selected from the group consisting of hydrogen; a halogen; amino; nitro; cyano; formyl; carboxyl; a $C_{1-10}$ alkyl substituted or unsubstituted with one or more substituents selected from the group consisting of a halogen, hydroxyl, amino, cyano, nitro, and a $C_{6-10}$ aryl; a $C_{1-10}$ alkylcarbonyl; a $C_{6-10}$ aryl; and a $C_{1-10}$ alkoxy;

each of n and m independently represents an integer of from 0 to 5; and each of $R_1$ and $R_2$ independently represents a $C_{1-5}$ straight or branched alkyl substituted or unsubstituted with a halogen or OH; a $C_{3-10}$ cycloalkyl substituted or unsubstituted with a halogen or OH; a $C_{2-5}$ straight or branched alkenyl substituted or unsubstituted with a halogen or OH; a $C_{2-5}$ straight or branched alkynyl substituted or unsubstituted with a halogen or OH; or an aryl substituted or unsubstituted with a halogen or OH.

In accordance with an embodiment of the present disclosure, the optical resolution method may include an enantioselective liquid-liquid extraction (ELLE) process, but may not be limited thereto.

In accordance with an embodiment of the present disclosure, the t-butylketone binaphthol derivative may optically convert a D-amino acid into a L-amino acid, or optically convert a L-amino acid into a D-amino acid, but may not be limited thereto.

In accordance with an embodiment of the present disclosure, the optical resolution method may be ascribed to a difference in stability of an imine compound formed by binding the t-butylketone binaphthol derivative with an amine group from an amino acid, but may not be limited thereto.

The t-butylketone binaphthol derivative of the present disclosure includes a carbonyl group (C=O) which is a functional group that can react with various amine groups to form an imine, and the optical resolution is ascribed to a difference in stability of the imine compound. An example of alpha amino acids which can be optically resolved by the t-butylketone binaphthol derivative of the present disclosure may be represented by the following Chemical Formula 3 which include an L- or D-optical isomer due to an chiral carbon within the molecule:

NH$_2$CHR$_3$COOH;  [Chemical Formula 3]

in the above Chemical Formula 3, R$_3$ is a halogen or a monovalent organic group except for hydrogen, and desirably a substituted or unsubstituted alkyl, a substituted or unsubstituted alkenyl, a substituted or unsubstituted cycloalkyl, or a substituted or unsubstituted aryl.

The t-butylketone binaphthol derivative of the present disclosure can optically resolve beta amino acids. An example of the beta amino acids may be an amino acid represented by the following Chemical Formula 4, but may not be limited thereto:

NH$_2$R$_4$CHCH$_2$COOH;  [Chemical Formula 4]

in the above Chemical Formula 4, R$_4$ is independently a halogen or a monovalent organic group except for hydrogen, and desirably a substituted or unsubstituted alkyl, a substituted or unsubstituted alkenyl, a substituted or unsubstituted cycloalkyl, or a substituted or unsubstituted aryl.

A S-optical isomer of the t-butylketone binaphthol derivative represented by Chemical Formula 1 of the present disclosure selectively extracts a D-amino acid, and its R-optical isomer selectively extracts a L-amino acid.

MODE FOR CARRYING OUT THE INVENTION

Hereinafter, examples will be described in more detail with reference to the accompanying drawings. However, the following examples are provided only for more easily understanding of the present disclosure, but the present disclosure is not limited thereto.

EXAMPLES

Example 1: Synthesis of Compound (S)-1

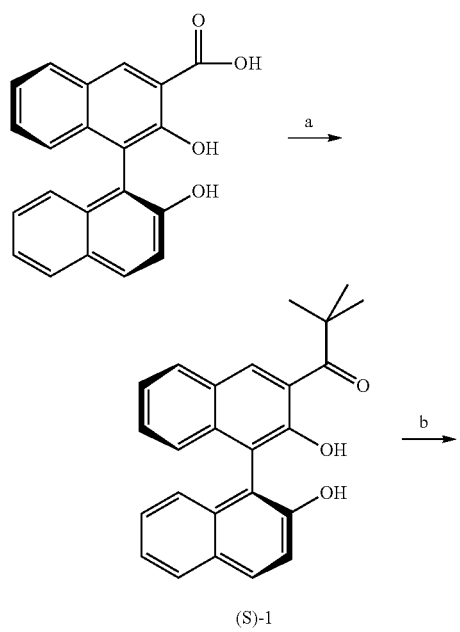

(S)-1

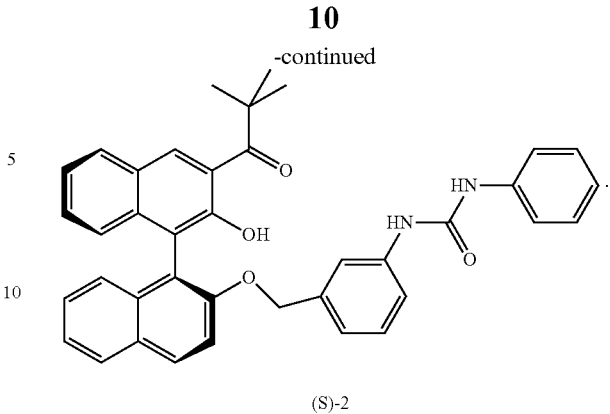

(S)-2 t-Butyllithium (1.6 M in hexane, 31 mL, 50 mmol) was dropwisely added at 0° C. to a solution in which (S)-2-carboxyl-1,1'-binaphthalene-2,2'-diol (3.3 g, 10 mmol) was dissolved in THF (20 mL). After stirring the solution at room temperature for 12 hours, a NH$_4$Cl saturated aqueous solution was added to the reaction solution to end the reaction, and THF was vacuum-distilled out. A remaining product was extracted using water and ethyl acetate (EA) (3×25 mL). The product obtained by drying an organic layer with MgSO$_4$ and vacuum-distilling the solution was subject to column chromatography using EA/hexane (1/7) so as to obtain a compound (S)-1 (2.7 g, 73%): $^1$H NMR (300 MHz, CDCl$_3$) δ 11.65 (s, 1H), 8.81 (s, 1H), 7.9-8.1 (m, 3H), 7.1-7.5 (m, 7H), 5.24 (s, 1H), 1.65 (s, 9H).

Example 2: Synthesis of Compound (S)-2

NaH (60%, 0.25 g, 6.3 mmol) was put into a DMF solution (20 mL) in which the compound (S)-1 (2.3 g, 6.2 mmol) was dissolved, and then stirred at 0° C. for 2 hours. 3-phenylureyl-benzyl bromide (2.1 g, 6.3 mmol) was added thereto. After stirring the solution at room temperature for 15 hours, NH$_4$Cl was added to end the reaction, and the remaining product was extracted using EA and water. An organic layer was washed sufficiently with water, the EA was vacuum-distilled, and a compound (S)-2 (1.7 g, yield: 45%) was obtained through column chromatography (eluent: EA/hexane 1/5): $^1$H NMR (300 MHz, dmso-d$^6$) δ 9.19 (s, 1H), 8.71 (s, 1H), 8.70 (s, 1H), 7.16 (d, 1H), 7.95-8.05 (m, 3H), 7.67 (d, 1H), 6.65-7.55 (m, 16H), 5.13 (s, 2H), 1.25 (s, 9H).

Test Example 1: Chiral Extraction Effect Test of Compound (S)-2 on Phenylalanine Aliquat 336 (1.05 eq) was put into a methylene chloride solution (10 mM, 5 mL) of the compound (S)-2, and then liquid-liquid extraction reaction with a phenylalanine aqueous solution (250 mM, 5 mL, pH 11.0) was conducted: The $^1$H NMR spectra in FIG. 1A to FIG. 1C show the results of the liquid-liquid extraction test.

FIG. 1A shows a spectrum of an organic layer obtained after the liquid-liquid extraction with pure L-phenylalanine at room temperature for 3 hours. It can be seen from the benzyl —CH$_2$— peak between 5 ppm and 5.5 ppm that some imines were formed between the (S)-2 and the L-Phe and more parts were present in a free form. Even when the reaction was conducted for a longer time, there was no increase in an amount of the imine.

Figure 1B:
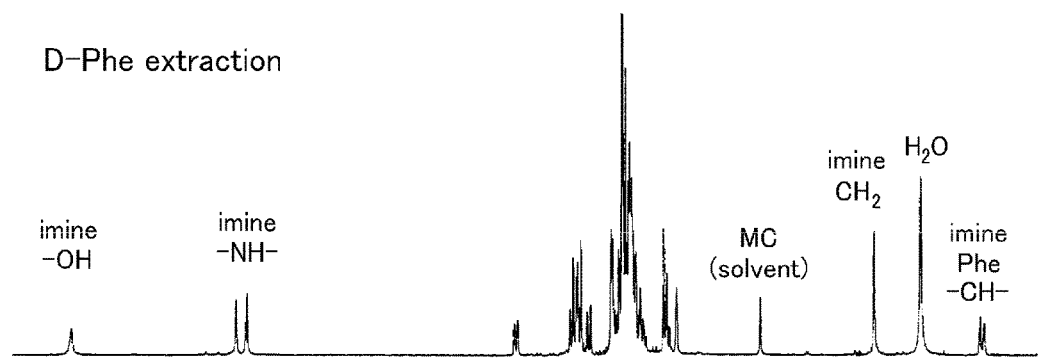
FIG. 1B shows a $^1$H NMR spectrum of an organic layer after liquid-liquid extraction of an aqueous solution layer using D-Phe only in an ELLE experiment with phenylalanine in accordance with an example of the present disclosure

On the other hand, FIG. 1B shows a spectrum after the liquid-liquid extraction with pure D-phenylalanine at room temperature for 3 hours. It can be seen that imine 2-D-Phe obtained by the reaction between the D-phenylalanine and the (S)-2 was produced with a high yield. The peak at 11.95 ppm corresponds to —OH which appears at a very downfield due to the nitrogen and hydrogen bond to form the imine. The peaks at 10.52 ppm and 10.45 ppm correspond to two free NH's which also appear at a downfield since they participate in the strong hydrogen bonding with phenylalanine-$CO_2$ in the imine. Further, the peak at 5.15 ppm corresponds to benzyl $CH_2$ of the imine, and the peak at 4.24 ppm is caused by phenylalanine alpha hydrogen in the imine. As a result, FIG. 1B shows that the imine was formed well.

Figure 1C:
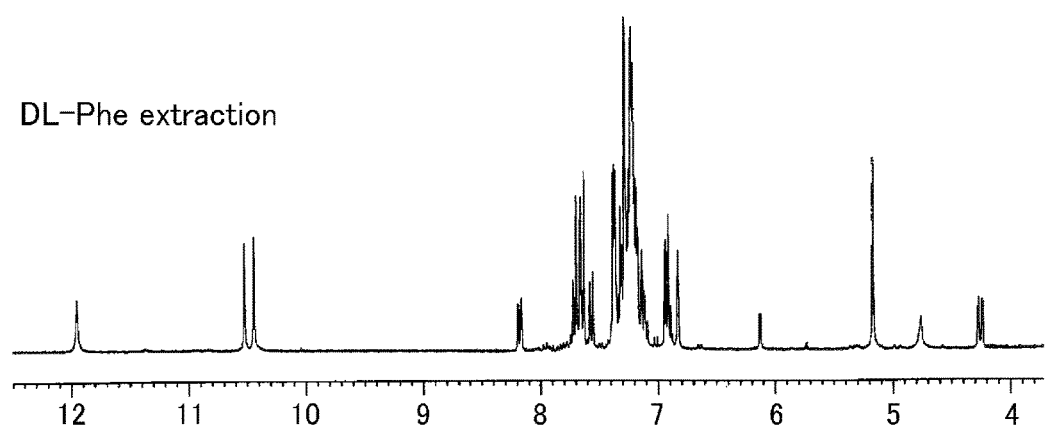
FIG. 1C shows a $^1$H NMR spectrum of an organic layer after liquid-liquid extraction of an aqueous solution layer using DL-Phe in an ELLE experiment with phenylalanine in accordance with an example of the present disclosure.

FIG. 1C shows a $^1$H NMR spectrum of an organic layer after the liquid-liquid extraction with racemic phenylalanine and is surprisingly similar to FIG. 1B. This means that only D-phenylalanine from the racemic phenylalanine in the aqueous solution layer forms an imine with the (S)-2 in the organic layer. That is, the (S)-2 is a chiral extracting agent having a significantly high chiral selectivity with respect to D-phenylalanine.

Test Example 2: Theoretical Basis for Chiral Selectivity

Figure 2:
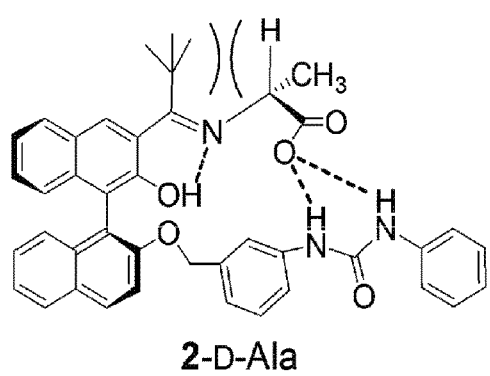
FIG. 2 are structural formulas showing hydrogen bonding and steric hindrance in 2-D-Ala on the left and 2-L-Ala on the right in accordance with an example of the present disclosure.
Figure 2:
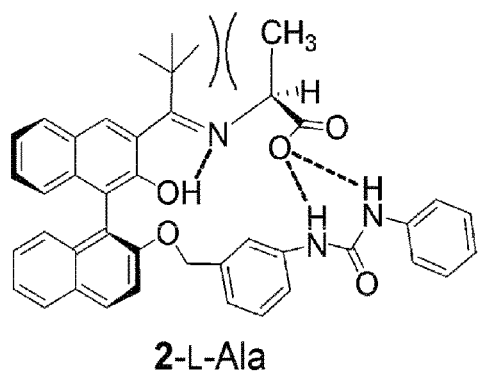

The minimum energy estimate structures of imines 2-L-Ala and 2-D-ala formed by reactions with basic amino acids D-alanine and L-alanine were calculated using the Spartan program. As a result, hydrogen bonding as shown in FIG. 2 can be predicted. This hydrogen bonding results in strong steric hindrance between —$CH_3$ group from the amino acid and t-butyl ring from the (S)-2 in the 2-L-Ala. In case of the 2-D-Ala, steric hindrance is formed between —H from the amino acid and t-butyl ring from the (S)-2, and it is a relatively a weak steric hindrance. As a result, the 2-D-Ala became a more stable state than the 2-L-Ala.

The chiral selectivity for amino acids was already explained on the basis of the above-described theory in the article published in 2007. However, according to the previously published articles, it was not easy to predict that the compound (S)-2 of the present disclosure would really have an excellent chiral selectivity as shown in the present disclosure. The chiral selectivity shown in the present example is regarded far more than the predictions of the previous publications.

Liquid-liquid extraction test was conducted to other general natural amino acids in the same manner as conducted with phenylalanine described above, and the results thereof were as shown in Table 1. It can be seen from Table 1 that the (S)-2 forms an imine with a high selectivity, i.e., ee value of 99% or more, with respect to the six amino acids. However, the (S)-2 had a low imine yield and an unclear or poor selectivity with respect to seine, threonine, and cysteine.

As can be seen from Table 1, the amino acids having a hydrophobic side chain were extracted well with a high selectivity under the liquid-liquid extraction conditions with respect to the (S)-2. It is considered that besides the amino acids listed in Table 1, all of amino acids having a hydrophobic side chain can be successfully applied to the enantioselective liquid-liquid extraction (ELLE) using the (S)-2 as an extracting agent.

TABLE 1

| Entry | Substrate | Yield [b] (%) | ee (%) [c] |
|---|---|---|---|
| 1 | Phe | 97% | >99 |
| 2 | Ala | 85% | 84 |
| 3 | Ile | 90% | >99 |
| 4 | Leu | 95% | >99 |
| 5 | Met | 90% | >99 |
| 6 | Trp | 88% | >99 |
| 7 | Val | 87% | >99 |
| 8 | Thr | 10% | unclear |
| 9 | Cys | 98% | 5 |
| 10 | Ser | 5% | unclear |

Table 1 shows imine yields and ee values of amino acids in an imine state measured by $^1$H NMR when ELLE was performed using the (S)-2 as an extracting agent under the conditions of an organic layer 10 mM (S)-2+1.05 eq. Aliquat 336; an aqueous solution layer 250 mM, amino acid sodium salt, room temperature, and 3 h to 20 h.

The compound (S)-3 represented by the following Chemical Formula 5, which is disclosed as a binol compound having a hydroxyl phenyl ketone group in the previous invention, showed a high selectivity (Korean Patent Application No. 10-2012-0098636). However, as for the (S)-3, the entire organic layer needs to be evaporated and then treated with a methanol-HCl solution to hydrolyze an imine formed after liquid-liquid extraction of an amino acid, which results in an increase in the process cost. Meanwhile, as for the (S)-2 of the present disclosure, an organic layer obtained after liquid-liquid extraction is well hydrolyzed by treating it with a HCl-aqueous solution layer, and the organic layer after the hydrolysis remains in its initial state and thus can be reused in other extraction processes, which is an advantage in that the process cost can be greatly reduced.

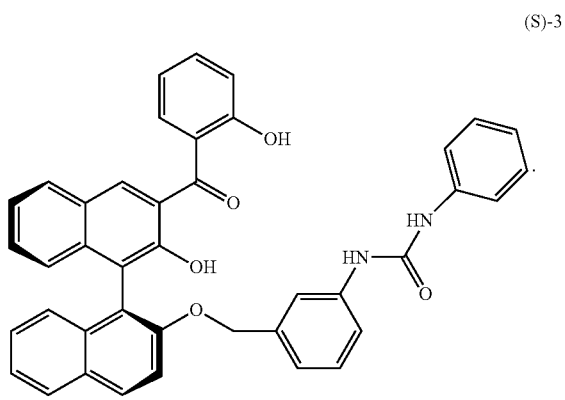

(S)-3

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A t-butylketone binaphthol compound of the following Chemical Formula 1:

[Chemical Formula 1]

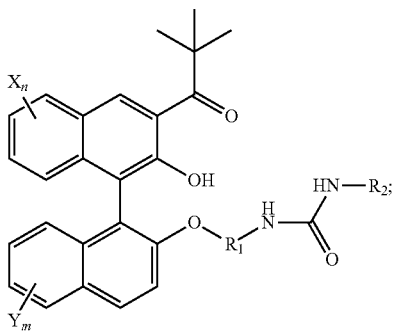

wherein in the above Chemical Formula 1,
X is independently selected from the group consisting of hydrogen; a halogen; amino; nitro; cyano; formyl; carboxyl; a $C_{1-10}$ alkyl substituted or unsubstituted with one or more substituents selected from the group consisting of a halogen, hydroxyl, amino, cyano, nitro, and a $C_{6-10}$ aryl; a $C_{1-10}$ alkylcarbonyl; a $C_{6-10}$ aryl; and a $C_{1-10}$ alkoxy;
Y is independently selected from the group consisting of hydrogen; a halogen; amino; nitro; cyano; formyl; carboxyl; a $C_{1-10}$ alkyl substituted or unsubstituted with one or more substituents selected from the group consisting of a halogen, hydroxyl, amino, cyano, nitro, and a $C_{6-10}$ aryl; a $C_{1-10}$ alkylcarbonyl; a $C_{6-10}$ aryl; and a $C_{1-10}$ alkoxy;
each of n and m independently is an integer from 0 to 5; and
each of $R_1$ and $R_2$ independently is a $C_{1-5}$ straight or branched alkyl substituted or unsubstituted with a halogen or OH; a $C_{3-10}$ cycloalkyl substituted or unsubstituted with a halogen or OH; a $C_{2-5}$ straight or branched alkenyl substituted or unsubstituted with a halogen or OH; a $C_{2-5}$ straight or branched alkynyl substituted or unsubstituted with a halogen or OH; or an aryl substituted or unsubstituted with a halogen or OH.

2. The t-butylketone binaphthol compound of claim 1, wherein the t-butylketone binaphthol compound is a compound of the following Chemical Formula 2:

[Chemical Formula 2]

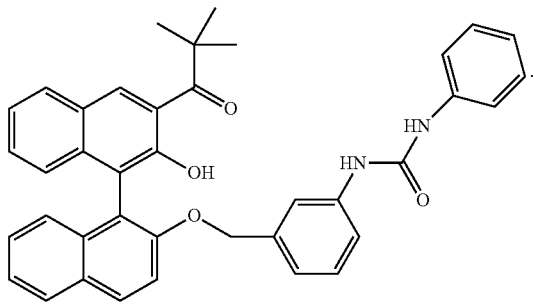

3. A chiral extracting agent comprising the t-butylketone binaphthol compound of claim 1.
4. The chiral extracting agent of claim 3, wherein the t-butylketone binaphthol compound has a chiral selectivity of 95% or more.
5. The chiral extracting agent of claim 3, wherein the t-butylketone binaphthol compound is in a S-form or R-form.
6. The chiral extracting agent of claim 3, wherein the t-butylketone binaphthol compound is used for L/D optical conversion of an amino acids.
7. An optical resolution method of a racemic amino acid, comprising: exposing said racemic amino acid to an extracting agent including a t-butylketone binaphthol compound of the following Chemical Formula 1:

[Chemical Formula 1]

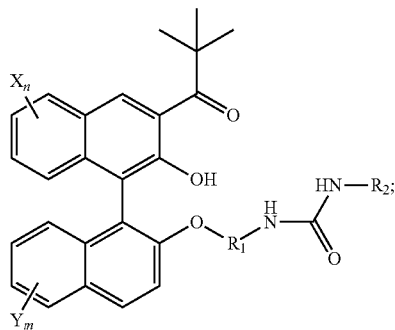

wherein in the above Chemical Formula 1,
X is independently selected from the group consisting of hydrogen; a halogen; amino; nitro; cyano; formyl; carboxyl; a $C_{1-10}$ alkyl substituted or unsubstituted with one or more substituents selected from the group consisting of a halogen, hydroxyl, amino, cyano, nitro, and a $C_{6-10}$ aryl; a $C_{1-10}$ alkylcarbonyl; a $C_{6-10}$ aryl; and a $C_{1-10}$ alkoxy;
Y is independently selected from the group consisting of hydrogen; a halogen; amino; nitro; cyano; formyl; carboxyl; a $C_{1-10}$ alkyl substituted or unsubstituted with one or more substituents selected from the group consisting of a halogen, hydroxyl, amino, cyano, nitro, and a $C_{6-10}$ aryl; a $C_{1-10}$ alkylcarbonyl; a $C_{6-10}$ aryl; and a $C_{1-10}$ alkoxy;
each of n and m independently is an integer from 0 to 5; and
each of $R_1$ and $R_2$ independently is a $C_{1-5}$ straight or branched alkyl substituted or unsubstituted with a halogen or OH; a $C_{3-10}$ cycloalkyl substituted or unsubstituted with a halogen or OH; a $C_{2-5}$ straight or branched alkenyl substituted or unsubstituted with a halogen or OH; a $C_{2-5}$ straight or branched alkynyl substituted or unsubstituted with a halogen or OH; or an aryl substituted or unsubstituted with a halogen or OH.

8. The optical resolution method of racemic amino acids of claim 7, wherein the optical resolution method includes an enantioselective liquid-liquid extraction (ELLE) process.
9. The optical resolution method of racemic amino acids of claim 7, wherein the t-butylketone binaphthol compound optically converts a D-amino acid into a L-amino acid, or optically converts a L-amino acid into a D-amino acid.

* * * * *